US006165506A

United States Patent [19]
Jain et al.

[11] Patent Number: 6,165,506
[45] Date of Patent: Dec. 26, 2000

[54] SOLID DOSE FORM OF NANOPARTICULATE NAPROXEN

[75] Inventors: Rajeev A. Jain, Norristown; Linden Wei, Exton; Jon Swanson, North Wales, all of Pa.

[73] Assignee: Elan Pharma International Ltd., Co. Clare, Ireland

[21] Appl. No.: 09/148,332

[22] Filed: Sep. 4, 1998

[51] Int. Cl.[7] .............................. A61K 9/46; A61K 9/14; A61L 9/04; A01N 37/10
[52] U.S. Cl. ............................ 424/466; 424/43; 424/44; 424/464; 424/465; 514/569
[58] Field of Search .............................. 424/43, 44, 489, 424/464, 466, 465; 514/569

[56] References Cited

U.S. PATENT DOCUMENTS

| | | | |
|---|---|---|---|
| 3,904,682 | 9/1975 | Fried et al. | 260/520 |
| 4,009,197 | 2/1977 | Fried et al. | 260/473 |
| 4,780,320 | 10/1988 | Baker | 424/493 |
| 4,824,664 | 4/1989 | Tarral et al. | . |
| 4,888,178 | 12/1989 | Rotini et al. | 424/468 |
| 4,919,939 | 4/1990 | Baker | 424/493 |
| 4,940,588 | 7/1990 | Sparks et al. | 424/490 |
| 4,952,402 | 8/1990 | Sparks et al. | 424/419 |
| 5,145,684 | 9/1992 | Liversige et al. | 424/489 |
| 5,200,193 | 4/1993 | Radebaugh et al. | 424/468 |
| 5,354,556 | 10/1994 | Sparks et al. | 424/419 |
| 5,462,747 | 10/1995 | Radebaugh et al. | 424/465 |
| 5,480,650 | 1/1996 | Marchi et al. | 424/464 |
| 5,565,188 | 10/1996 | Wong et al. | . |
| 5,591,456 | 1/1997 | Franson et al. | 424/494 |

OTHER PUBLICATIONS

Boylan et al., American Association Production Staff, Library of Congress, (1986), 2 pages.
Budavari et al., The Merck Index, National Institutes of Health, (1990), p. 1014.
Gennaro, "Oral Solid Dosage Forms," *Remington's Pharmaceutical Sciences.*, Chapter 89 1633–41 (1990).
Kristensen et al., "Relief of Pain and Trismus in Patients Treated with Naproxen or Acetylsalicylic Acid After Tonsillectomy", *J. Laryngol Otol.*, 102 (1):39–42 (1988).
Hespe et al., "Bioavailability of New Formulations of Amoxicillin in Relation to its Absorption Kinetics", *Arzneimittelforschung*, 37 (3): 372–5 (1987).
Spitz, "Determination of Water in Aluminum Chlorohydrate and Effervescent Tablets by Karl Fischer Analysis", *J. Pharm Sci.*, 68(1): 122–3 (1979).
Ross–Lee et al., Plasma Levels of Aspirin Following Effervescent and Enteric Coated Tablets, and Their Effect on Platelet Function, *Eur J. Clin Pharmacol*, 23 (6): 545–51 (1982).
Nishimura et al., "Dosage Form Design for Improvement of Bioavailability of Levodopa VI: Formulation of Effervescent Enteric–Coated tablets", *J. Pharm Sci.*, 73(7): 942–6 (1984).
Sendall et al., "A Study of Powder Adhesion to Metal Surfaces During Compression of Effervescent Pharmaceutical Tablets", *J. Pharm. Pharmacol.*, 38(7): 489–93 (1986).

*Primary Examiner*—Thurman K. Page
*Assistant Examiner*—Brian K. Seidleck
*Attorney, Agent, or Firm*—Foley & Lardner

[57] ABSTRACT

Described are solid dose nanoparticulate naproxen formulations having high rates of dissolution. The solid dose nanoparticulate naproxen formulations can comprise an alkali compound, which functions to increase the dissolution rate of the naproxen following administration. Alternatively, the solid dose nanoparticulate naproxen formulation can comprise an alkali compound and an acidic compound, which can react together to form carbon dioxide. The formed carbon dioxide can also aid in increasing the dissolution rate of the naproxen following administration. Also described are solid dose nanoparticulate naproxen formulations having a decreased concentration of a binder/disintegrant agent. Such compositions also provide an increased rate of dissolution of naproxen following administration.

21 Claims, No Drawings

SOLID DOSE FORM OF NANOPARTICULATE NAPROXEN

BACKGROUND OF THE INVENTION

1. Field of the Invention

The present invention is directed to new solid dose forms of nanoparticulate naproxen having improved dissolution rates, methods of making such formulations, and methods of using such formulations.

2. Description of the Related Art

Naproxen, also known as (S)-6-methoxy-α-methyl-2-napthaleneacetic acid and d-2-(6-methoxy-2-naphthyl) propionic acid, is a well-known anti-inflammatory, analgesic, and antipyretic agent. It has been approved in many countries around the world for almost two decades and has a very safe risk-benefit profile. It is sold under the trade names ALEVE® (distributed by Bayer), ANAPROX®, NAPROSYN®, and SYNFLEX® (all manufactured by Roche Laboratories, Inc.). See The Merck Index, 11$^{th}$ Edition, pp. 6330 (Merck & Co., Rahway, N.J., 1989).

Naproxen, which is highly water insoluble, i.e., less than 10 mg/ml, has the following chemical structure:

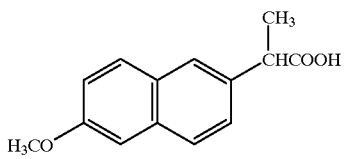

The degree and timing in which a drug becomes available to the target tissue after administration is determined by many factors, including the dosage form and various properties, e.g. dissolution rate, of the drug. Poor onset of action is a significant problem encountered in the development of pharmaceutical compositions, particularly those containing an active ingredient that is poorly soluble in water, such as naproxen. Poorly water soluble drugs tend to be eliminated from the gastrointestinal tract before being absorbed into the circulation, and tend to have an extended period following administration prior to onset of action.

The dissolution rate of a particulate drug can increase with increasing surface area, i.e., decreasing particle size. An increased dissolution rate can lead to a faster onset of action. Consequently, methods of making finely divided drugs have been studied and efforts have been made to control the size and size range of drug particles in pharmaceutical compositions. Methods of making nanoparticulate compositions are described in U.S. Pat. No. 5,145,684 for "Surface Modified Drug Nanoparticles," hereby specifically incorporated by reference.

Another method for increasing the rate of disintegration of a solid-dose formulation of a drug includes the use of effervescent tablets. In addition to the drug substance, effervescent tablets contain sodium bicarbonate and an organic acid, such as tartaric or citric. In the presence of water, these additives react liberating carbon dioxide which acts as a disintegrator and produces effervescence. Gennaro, ed., Remington's, 14$^{th}$ Edition, page 1634 (Mack Publishing Co., 1990). Exemplary compounds that have been formulated as effervescent tablets include aspirin and naproxen (Ross-Lee et al., "Plasma Levels of Aspirin Following Effervescent and Enteric Coated Tablets, and Their Effect on Platelet Function, Eur. J. Clin. Pharmacol., 23:545–51 (1982); Kristensen et al., "Relief of Pain and Trismus in Patients Treated with Naproxen or Acetylsalicylic Acid After Tonsillectomy," J. Laryngol. Otol., 102:39–42 (1988)); levodopa (Nishimura et al., "Dosage Form Design for Improvement of Bioavailability of Levodopa VI: Formulation of Effervescent Enteric-coated Tablets," J. Pharm. Sci., 73:942–6 (1984)), and amoxicillin (Hespe et al., "Bioavailability of New Formulations of Amoxicillin in Relation to its Absorption Kinetics," Arzneimittelforschungf, 37:372–5 (March, 1987)).

Naproxen is a non-steroidal anti-inflammatory drug (NSAID) often used to relieve the inflammation, swelling, stiffness, and joint pain associated with rheumatoid arthritis, osteoarthritis (the most common form of arthritis), juvenile arthritis, ankylosing spondylitis (spinal arthritis), tendinitis, bursitis, and acute gout. In addition, it is used to treat pain associated with menstrual periods, migraine headaches, and other types of mild to moderate pain.

Naproxen is a more potent pain reliever than aspirin, especially for menstrual cramps, toothaches, minor arthritis, and injuries accompanied by inflammation, such as tendinitis. The naproxen sodium salt is specifically indicated in the treatment of various types of acute and very high intensity pain because it induces a rapid and sustained remission. In addition, it is possible to obtain a good analgesic effect with few administrations, due to naproxen's particular pharmacokinetics. Tablet formulations of naproxen were approved for OTC ("over the counter" as compared to prescription) marketing by the U.S. Food and Drug Administration in 1994.

Naproxen acts by suppressing the production of prostaglandins, which are hormone-like substances that act on local tissues to produce pain and inflammation. Its pharmaceutical forms of delivery include tablets, capsules, and liquids. Delivery characteristics and forms are disclosed in, for example, U.S. Pat. Nos. 3,904,682; 4,009,197; 4,780,320; 4,888,178; 4,919,939; 4,940,588; 4,952,402; 5,200,193; 5,354,556; 5,462,747; and 5,480,650, all of which are specifically incorporated by reference. The synthesis of naproxen is described in, for example, U.S. Pat. Nos. 3,904,682 and 4,009,197, both of which are specifically incorporated by reference.

There is currently a need for naproxen formulations having a faster rate of dissolution following administration and which, therefore, likely have a faster onset of action. In addition, there is a need in the art for methods of making and methods of using such naproxen formulations. The present invention satisfies these needs.

SUMMARY OF THE INVENTION

The present invention is directed to the surprising and unexpected discovery of a new solid dose form of nanoparticulate naproxen having improved dissolution characteristics over prior macro-sized and nanoparticulate solid dose formulations of naproxen. It is believed that the increased dissolution rate results in a faster onset of action following administration. Nanoparticulate compositions were first described in U.S. Pat. No. 5,145,684 ("the '684 patent"), which is specifically incorporated herein by reference.

This is an improvement over co-owned pending application No. 08//800,006 for "Formulations of Nanoparticulate Naproxen Tablets," and over co-owned U.S. Pat. No. 5,591,456 for "Milled Naproxen with Hydroxypropyl Cellulose as a Dispersion Stabilizer," issued on Jan. 7, 1997, the disclosures of which are specifically incorporated by reference.

The new solid dose naproxen formulations comprise nanoparticulate naproxen, having an effective average particle size of less than about 600 nm, and a surface modifier adsorbed on the surface thereof. Preferably, the effective average particle size of the nanoparticulate naproxen is less than about 450 nm, more preferably less than about 300 nm, even more preferably less than about 250 nm, and most preferably less than about 100 nm.

The improvement comprises adding an alkali agent to the solid dose composition. It is believed that the alkali agent functions to raise the pH of the dissolution microenvironment surrounding the naproxen, thereby increasing the dissolution rate of the naproxen composition following administration of the drug. This modification unexpectedly produces a composition having dramatically improved dissolution characteristics and, consequently, most likely a faster onset of action.

In another embodiment of the invention, an acidic agent, in addition to the alkali agent, is added to the solid dose nanoparticulate naproxen composition. The acidic agent reacts with the alkali agent to produce carbon dioxide, which acts as a disintegrant to increase the dissolution rate of naproxen.

The present invention is also directed to solid dose nanoparticulate naproxen compositions having a decreased concentration of a binder/disintegrant agent as compared to that taught in the prior art, which results in a nanoparticulate composition having an increased rate of dissolution.

A wetting agent can also be added to any of the modified solid dose naproxen formulations to aid in the increase of the dissolution rate of the drug.

Yet another aspect of the present invention provides a method of treating a mammal requiring anti-inflammatory, analgesic, or antipyretic treatment comprising administering to the mammal one or more of the above-described solid dose nanoparticulate naproxen formulations.

In another aspect of the invention there is provided a method of preparing solid dose nanoparticulate naproxen formulations having rapid dissolution characteristics. The method comprises one or more of the following: (1) adding an alkali compound to a solid dose nanoparticulate naproxen formulation; (2) adding an alkali compound and an acidic compound to a solid dose nanoparticulate naproxen formulation; and (3) decreasing the concentration of a binder/disintegrant agent from that taught in prior art directed to nanoparticulate solid dose naproxen compositions. A wetting agent can be added to any of these formulations to increase the rate of disintegration of the solid dose formulation.

It is to be understood that both the foregoing general description and the following detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF THE INVENTION

The present invention is directed to the surprising and unexpected discovery of new solid dose formulations of naproxen having improved dissolution characteristics following administration. The solid dose nanoparticulate naproxen compositions comprise naproxen having an effective average particle size of less than about 600 nm with a surface modifier adsorbed on the surface thereof. Preferably, the effective average particle size of the nanoparticulate naproxen is less than about 450 nm, more preferably less than about 300 nm, even more preferably less than about 250 nm, and most preferably less than about 100 nm.

A. Preferred Solid Dose Forms of Naproxen

Naproxen is a weak acid, highly soluble in alkaline conditions. It was surprisingly discovered that by adding an alkali agent to the solid dose formulation, the dissolution rate of the solid dose formulation is dramatically increased. It is believed that the alkali agent functions to increase the pH of the microenvironment surrounding the drug during dissolution following administration, and thereby increases the naproxen rate of dissolution. Exemplary pharmaceutically acceptable alkali compounds that can be added to a solid dose form of nanoparticulate naproxen include sodium bicarbonate and potassium bicarbonate. The alkali agent is preferably present in an amount of from about 3.0 to about 40%, by weight, and more preferably from about 5.0 to about 10%, by weight.

It was discovered that by increasing the pH of the dissolution medium, for example from about 6.0 to about 7.4, the dissolution rate of naproxen increased by up to over 3-fold as compared to macro-sized formulations of naproxen (ALEVE® (Roche)), and up to 30% over the dissolution rate of prior solid dose nanoparticulate naproxen formulations.

Another aspect of the invention encompasses adding an acidic agent, in addition to the alkali agent when the alkali agent is a bicarbonate agent, to the solid dose form of nanoparticulate naproxen. The acidic agent reacts with the alkali agent to produce carbon dioxide. This evolved carbon dioxide may act as a secondary disintegrating agent, causing rapid disintegration of the solid dose form of nanoparticulate naproxen and subsequent faster dissolution of the drug. Exemplary pharmaceutically acceptable acidic agents include citric acid, anhydrous citric acid, fumaric acid, tartaric acid, and malic acid. The acidic agent is preferably present in an amount of from about 0.3 to about 4.0%, by weight, and more preferably from about 0.2 to about 2.0%, by weight.

Bicarbonate compounds are preferred as the alkali agent, as they can react with an acidic compound to form carbon dioxide, resulting in an "effervescent" tablet. However, if an acidic agent is not added to the solid dose form of nanoparticulate naproxen, any pharmaceutically acceptable alkali compound can be used to obtain a solid dose form of naproxen having increased dissolution characteristics.

The invention is also directed to solid dose nanoparticulate naproxen compositions having a lower concentration of a binder/disintegrant as compared to that taught in the prior art, producing a composition having an increased rate of dissolution. The concentration of the binder/disintegrant agent can vary from about 0.1 to about 10%, and preferably is from about 0.5 to about 8%, and more preferably from about 1.0 to about 6.0%, by weight.

A wetting agent can also be added to the compositions of the invention to increase dissolution rates of the solid dose formulations. Exemplary wetting agents include pharmaceutically acceptable detergents, such as quaternary ammonium salts, or sodium lauryl sulfate, sucrose monolaurate, polyoxethylene monostearates, glyceryl triacetate, and magnesium lauryl sulfate. The wetting agent is preferably present in an amount of from about 0.5 to about 5%, by weight, and more preferably from about 1.0 to about 2%, by weight.

Pharmaceutical compositions comprising the modified forms of solid dose nanoparticulate naproxen are encompassed by the present invention. Such compositions comprise a modified form of solid dose nanoparticulate naproxen and a pharmaceutical excipient. Pharmaceutical compositions according to the present invention may also comprise binding agents, filling agents, lubricating agents, disintegrating agents, suspending agents, sweeteners, flavoring agents, preservatives, buffers, wetting agents, and other excipients.

B. Methods of Using Preferred Solid Dose Forms of Naproxen

The present invention provides a method of treating a mammal, including a human, requiring anti-inflammatory, analgesic, or antipyretic treatment comprising administering to the mammal a solid dose form of nanoparticulate naproxen as described above. Particularly advantageous features of the present invention include that because the pharmaceutical formulation of the invention exhibits unexpectedly rapid dissolution, it is likely to exhibit rapid onset of action following administration.

C. Methods of Preparing The Preferred Solid Dose Forms of Naproxen

Methods of preparing solid dose nanoparticulate naproxen formulations having rapid dissolution characteristics include one or more of the following: (1) adding an alkali compound to a solid dose nanoformulation of naproxen; (2) adding a bicarbonate alkali compound and an acidic compound to a solid dose nanoformulation of naproxen; and (3) decreasing the concentration of a binder/disintegrant agent from that taught in the prior art directed to nanoparticulate naproxen compositions.

The naproxen particles of this invention comprise a discrete crystalline phase of a drug substance having a surface modifier adsorbed on the surface thereof. The concentration of the primary surface modifier can vary from about 0.1 to about 50%, and preferably is from about 0.5 to about 20%, and more preferably from about 1.0 to about 10%, by weight. The concentration of naproxen can vary from about 30 to about 70% (w/w), and more preferably is from about 40 to about 60% (w/w).

Useful surface modifiers are believed to include those which physically adhere to the surface of the drug substance but do not chemically bond to the drug. Suitable surface modifiers are described in the '684 patent and in the *Handbook of Pharmaceutical Excipients,* published jointly by the American Pharmaceutical Association and The Pharmaceutical Society of Great Britain (The Pharmaceutical Press, 1986), the disclosure of which is hereby incorporated by reference in its entirety. The surface modifiers are commercially available and/or can be prepared by techniques known in the art.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants. Representative examples of excipients include gelatin, casein, lecithin (phosphatides), gum acacia, cholesterol, tragacanth, stearic acid, benzalkonium chloride, calcium stearate, glyceryl monostearate, cetostearl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, and polyvinylpyrrolidone (PVP). Most of these excipients are described in detail in the *Handbook of Pharmaceutical Excipients,* published jointly by the American Pharmaceutical Association and The Pharmaceutical Society of Great Britain, the Pharmaceutical Press, 1986.

Particularly preferred surface modifiers include polyvinyl pyrrolidone, Pluronic F68® and F108®, which are block copolymers of ethylene oxide and propylene oxide, Tetronic 908®, which is a tetrafunctional block copolymer derived from sequential addition of ethylene oxide and propylene oxide to ethylenediamine, dextran, lecithin, Aerosol OT®, which is a dioctyl ester of sodium sulfosuccinic acid, available from American Cyanamid, Duponol P®, which is a sodium lauryl sulfate, available from DuPont, Triton X-200®, which is an alkyl aryl polyether sulfonate, available from Rohm and Haas, Tween 80®, which is a polyoxyethylene sorbitan fatty acid ester, available from ICI Specialty Chemicals, and Carbowax 3350® and 934®, which are polyethylene glycols available from Union Carbide. Surface modifiers which have found to be particularly useful include polyvinylpyrrolidone, Pluronic F-68®, and lecithin.

The surface modifier is adsorbed on the surface of the drug substance in an amount sufficient to maintain an effective average particle size of less than about 600 nm. The surface modifier does not chemically react with the drug substance itself. Furthermore, the individually adsorbed molecules of the surface modifier are essentially free of intermolecular cross-linkages.

Preparation of nanoparticulate formulations are described in, for example, the '684 patent. In brief, the particle size of commercially-available macro-sized naproxen is reduced to the desired effective average particle size using a particle size reduction method. The naproxen particles can be reduced in size in the presence of a surface modifier, or the surface modifier can be added to the naproxen dispersion following particle size reduction.

The nanoparticulate naproxen formulations of the present invention are in a solid dose form. Such a solid dose form can be prepared by drying the nanoformulation of naproxen following grinding. A preferred drying method is spray drying. The spray drying process is used to obtain a nanoparticulate powder following the milling process used to transform the naproxen into nanoparticles. Such a nanoparticulate powder can be formulated into tablets for oral administration.

In an exemplary spray drying process, the high-solids naproxen nanosuspension and the surface modifier are fed to an atomizer using a peristaltic pump and atomized into a fine spray of droplets. The spray is contacted with hot air in the drying chamber resulting in the evaporation of moisture from the droplets. The resulting spray is passed into a cyclone where the powder is separated and collected. The spray dryer can be assembled in a co-current configuration with a rotary atomization nozzle and the nanosuspension can be fed to the rotary atomizer using a peristaltic pump. At the completion of the spray drying process, the collected spray-dried product comprises the naproxen nanoparticles suspended in a solid polymer matrix of the surface modifier.

The alkali agent, acidic agent, binding/disintegrant agent, and wetting agent are then added to the solid dose nanoformulation of naproxen to produce the desired preferred solid dose.

Particle Size

As used herein, particle size is determined on the basis of the weight average particle size as measured by conventional particle size measuring techniques well known to those skilled in the art. Such techniques include, for example, sedimentation field flow fractionation, photon correlation spectroscopy, light scattering, and disk centrifugation. By "an effective average particle size of less than about 600 nm" it is meant that at least 90% of the particles, by weight, have a particle size of less than about 600 nm when measured by the above-noted techniques. In preferred embodiments, the effective average particle size is less than about 450 nm, and more preferably less than about 400 nm. The naproxen particles can also have an effective average particle size of less than about 300 nm, less than about 250 nm, and less than about 100 nm. With reference to the effective average particle size, it is preferred that at least 90%, more preferably at least 95%, and most preferably at least 99% of the particles have a particle size less than the effective average particle size. In particularly preferred embodiments essentially all of the particles have a size less than about 600 nm.

The following examples are given to illustrate the present invention. It should be understood, however, that the invention is not to be limited to the specific conditions or details described in these examples.

EXAMPLE 1

The purpose of this example was to prepare modified forms of solid dose nanoparticulate naproxen.

Nanoparticulate naproxen spray-dried intermediate (SDI), comprising 93.0% (w/w) naproxen and 7.0% (w/w) polyvinylpyrrolidone (PVP) as the surface modifier, was used as standard nanoparticulate naproxen formulation.

Formulation 1, corresponding to the prior art solid dose nanoparticulate naproxen formulation, comprised 215 mg nanoparticulate naproxen SDI (200 mg naproxen, 15 mg PVP), 50.0 mg L-HPC (L-hydroxypropylcellulose) (Grade LH-11) (a weak binder/disintegrant), 150.0 mg fast flow lactose (Foremost #316) (excipient), and 1.0 mg magnesium stearate (excipient).

Modified forms of the standard base nanoparticulate naproxen formulation were prepared as follows. Formulation 2 comprised 215 mg nanoparticulate naproxen SDI (200 mg naproxen, 15 mg PVP), 25.0 mg L-HPC, 175.0 mg fast flow lactose, and 1.0 mg magnesium stearate. Formulation 3 comprised 215 mg nanoparticulate naproxen SDI (200 mg naproxen, 15 mg PVP), 25.0 mg L-HPC, 21 mg sodium bicarbonate (an alkali agent), 4 mg citric acid (an acidic agent), 150.0 mg fast flow lactose, and 1.0 mg magnesium stearate. Formulation 4 comprised 215 mg nanoparticulate naproxen SDI (200 mg naproxen, 15 mg PVP), 25.0 mg L-HPC, 15 mg sodium bicarbonate, 5 mg citric acid, 5 mg sodium lauryl sulfate (a wetting agent), 150.0 mg fast flow lactose, and 1.0 mg magnesium stearate,.

Formulations 1–4 were made into caplets using a Carver Press (5,000 lb., 10 sec.). The caplets were then tested for hardness (Erweka hardness tester), with all of the caplets exhibiting hardness in the range of 8–11 kP.

EXAMPLE 2

The purpose of this example was to compare the dissolution rate of the modified solid dose nanoparticulate naproxen with the dissolution rates of macro-sized naproxen (ALEVE®) and prior art solid dose nanoparticulate naproxen.

Formulations 1–4 were prepared as in Example 1. A summary of the four Formulations is provided below in Table 1.

TABLE 1

Naproxen Formulations

| Formulation No. | SDI | L-HPC | Fast Flow Lactose | Magnesium Stearate | Sodium Lauryl Sulfate | Sodium Bicarbonate | Citric Acid |
|---|---|---|---|---|---|---|---|
| 1 | 215 | 50.0 mg | 150.0 mg | 1.0 mg | — | — | — |
| 2 | 215 | 25.0 mg | 175.0 mg | 1.0 mg | — | — | — |
| 3 | 215 | 25.0 mg | 150.0 mg | 1.0 mg | — | 21 mg | 4 mg |
| 4 | 215 | 25.0 mg | 150.0 mg | 1.0 mg | 5 mg | 15 mg | 5 mg |

Dissolution Study

The in vitro dissolution (Distek dissolution system) of macro-sized naproxen (ALEVE®) was compared with the dissolution rates of the prior art and modified forms of solid dose nanoparticulate naproxen. For the dissolution study, the dissolution medium consisted of phosphate-buffer at 37° C., the pH of dissolution medium was 7.4, the rotation speed of the paddle of the Distek dissolution system was 50 rpm, and the detection wavelength was 332 nm.

Results

Table 2 shows the results of the dissolution comparison between the macro-sized naproxen (ALEVE®), prior art solid dose nanoparticulate naproxen (Formulation 1), and the modified solid dose nanoparticulate naproxen (Formulations 2, 3, and 4).

TABLE 2

Dissolution Comparison Results

| Formulation No. | Amount Naproxen Dissolved in 4.8 min. (%) |
|---|---|
| 1 | 64 |
| 2 | 70 |
| 3 | 92 |
| 4 | 73 |
| ALEVE ® (Roche) | 30 |

The addition of an alkali agent and an acidic agent to the solid dose form of nanoparticulate naproxen resulted in a composition having a remarkably increased rate of dissolution. Formulation 3, which differed from the prior art solid dose nanoparticulate naproxen Formulation 1 in the addition of an alkali agent (sodium bicarbonate) and an acidic agent (citric acid), surprisingly showed a dissolution rate of 92% in 4.8 minutes, as compared to the dissolution rate of 64% for Formulation 1 and 30% for ALEVE®—a 45% and 207% increase, respectively. Similarly, Formulation 4, which differed from the prior art solid dose nanoparticulate naproxen Formulation 1 in the addition of an alkali agent (sodium bicarbonate), an acidic agent (citric acid), and a wetting agent (sodium lauryl sulfate), showed a dissolution rate of 73% in 4.8 minutes, as compared to the dissolution rate of 64% for Formulation 1 and 30% for ALEVE®—a 14% and 143% increase, respectively.

It is believed that the alkali agent (sodium bicarbonate) functions to increase the pH of the microenvironment surrounding naproxen during dissolution, thereby increasing naproxen's rate of dissolution. In addition, the alkali agent (sodium bicarbonate) is likely reacting with the acidic agent (citric acid) to produce carbon dioxide. This evolved carbon dioxide may be acting as a secondary disintegrating agent, causing rapid disintegration of the tablet and subsequent faster dissolution of naproxen.

A decrease in the binder/disintegrant agent used in the caplet formulation also resulted in a dramatic increase in the dissolution rate of the solid dose nanoparticulate naproxen. Formulations 2, 3, and 4 all differed from the prior art solid dose nanoparticulate naproxen Formulation 1 in containing 50% less of the binder/disintegrant agent (25.0 mg of the binder/disintegrant, L-HPC, as compared to 50 mg for Formulation 1). Surprisingly, Formulations 2, 3, and 4 all showed dissolution rates (70, 92, and 73%, respectively) higher than that of Formulation 1 (64%) and higher than that of ALEVE® (30%). This may be because at low concentrations, i.e., about 5 to about 6%, the binder/disintegrant agent acts as a binder/disintegrant. However, at higher concentrations, i.e., about 11 to about 15%, the binder/disintegrant agent acts as a controlled-release (dissolution-rate limiting) polymer.

Finally, it was determined that addition of a wetting agent (sodium lauryl sulfate) also improved the dissolution of solid dose nanoparticulate naproxen. Formulation 4 differed from the prior art solid dose nanoparticulate naproxen (Formulation 1) in the addition of a wetting agent (sodium lauryl sulfate). Surprisingly, Formulation 4 showed a dissolution rate higher than that of Formulation 1 and that of ALEVE®—73% as compared to 64% and 30%, respectively.

It will be apparent to those skilled in the art that various modifications and variations can be made in the compositions, methods, and uses of the present invention without departing from the spirit or scope of the invention. Thus, it is intended that the present invention cover the modifications and variations of this invention provided they come within the scope of the appended claims and their equivalents.

We claim:

1. A solid dose nanoparticulate naproxen formulation having a high rate of dissolution comprising:
   (a) naproxen having an effective average particle size of less than about 600 nm;
   (b) polyvinylpyrrolidone adsorbed on the surface thereof, and
   (c) a pharmaceutically acceptable alkali agent, wherein following administration the alkali agent functions to increase the dissolution rate of the drug matrix surrounding the nanoparticulate naproxen in the solid dose formulation;
   wherein the solid dose formulation is made by:
      (1) preparing a nanoparticulate naproxen composition having polyvinylpyrrolidone adsorbed on the surface thereof;
      (2) drying the nanoparticulate naproxen composition;
      (3) adding to the dry nanoparticulate naproxen composition a pharmaceutically acceptable alkali agent; and
      (4) compressing the mixture of dry nanoparticulate naproxen, polyvinylpyrrolidone, and a pharmaceutically acceptable alkali agent to form a solid dose formulation.

2. The composition of claim 1, wherein the effective average particle size of the naproxen particles is selected from the group consisting of less than about 450 nm, less than about 400 nm, less than about 300 nm, less than about 250 nm, and less than about 100 nm.

3. The composition of claim 1, wherein the alkali agent is selected from the group consisting of sodium bicarbonate and potassium bicarbonate.

4. The composition of claim 3, wherein the alkali agent is present in an amount of from about 3.0 to about 40%, by weight.

5. The composition of claim 4, wherein the alkali agent is present in an amount of from about 5.0 to about 10%, by weight.

6. The composition of claim 1, further comprising a pharmaceutically acceptable acidic agent.

7. The composition of claim 6, wherein the acidic agent is selected from the group consisting of citric acid, anhydrous citric acid, fumaric acid, tartaric acid, and malic acid.

8. The composition of claim 7, wherein the acidic agent is present in an amount of from about 0.3 to about 4.0%, by weight.

9. The composition of claim 8, wherein the acidic agent is present in an amount of from about 0.2 to about 2.0%, by weight.

10. The composition of claim 1, further comprising a binder/disintegrant agent present in an amount of about 0.1 to about 10%, by weight.

11. The composition of claim 10, wherein the binder/disintegrant agent is present in an amount of about 0.5 to about 8.0%, by weight.

12. The composition of claim 11, wherein the binder/disintegrant agent is present in an amount of about 1.0 to about 6.0%, by weight.

13. The composition of claim 1, further comprising a pharmaceutically acceptable wetting agent.

14. The composition of claim 13, wherein said wetting agent is selected from the group consisting of sodium lauryl sulfate, sucrose monolaurate, polyoxethylene monostearates, glyceryl triacetate, and magnesium lauryl sulfate.

15. The composition of claim 14, wherein the wetting agent is present in an amount of from about 0.5 to about 5.0%, by weight.

16. The composition of claim 15, wherein the wetting agent is present in an amount of from about 1.0 to about 2.0%, by weight.

17. A method of preparing a solid dose nanoparticulate naproxen composition having a high rate of dissolution comprising:
   (a) preparing a nanoparticulate naproxen composition having polyvinylpyrrolidone adsorbed on the surface thereof, wherein the naproxen has an effective average particle size of less than about 600 nm;
   (b) drying the nanoparticulate naproxen composition;
   (c) adding to the dry nanoparticulate naproxen composition a pharmaceutically acceptable alkali agent, which functions to increase the dissolution rate of the nanoparticulate naproxen following administration; and
   (d) compressing the mixture of dry nanoparticulate naproxen, a surface modifier, and a pharmaceutically acceptable alkali agent to form a solid dose formulation,
wherein following administration the alkali agent functions to increase the dissolution rate of the drug matrix surrounding the nanoparticulate naproxen in the solid dose formulation.

18. The method of claim 17, further comprising adding a pharmaceutically acceptable acidic agent.

19. The method of claim 18, wherein the acidic agent is selected from the group consisting of citric acid, anhydrous citric acid, fumaric acid, tartaric acid, and malic acid.

20. The method of claim 17, further comprising adding a binder/disintegrant agent present in an amount of about 0.1 to about 10%, by weight.

21. A method of treating a mammal comprising administering to the mammal an effective amount of a solid dose nanoparticulate naproxen formulation having a high rate of dissolution, wherein the composition comprises:
   (a) naproxen particles having an effective average particle size of less than about 600 nm;
   (b) polyvinylpyrrolidone adsorbed on the surface of the naproxen particles;

(c) a pharmaceutically acceptable alkali agent, wherein following administration the alkali agent functions to increase the dissolution rate of the drug matrix surrounding the nanoparticulate naproxen in the solid dose formulation; and
(d) a pharmaceutically acceptable carrier, wherein the solid dose formulation is made by:
  (1) preparing a nanoparticulate naproxen composition having polyvinylpyrrolidone adsorbed on the surface thereof;
  (2) drying the nanoparticulate naproxen composition;
  (3) adding to the dry nanoparticulate naproxen composition a pharmaceutically acceptable alkali agent; and
  (4) compressing the mixture of dry nanoparticulate naproxen, polyvinylpyrrolidone, and a pharmaceutically acceptable alkali agent to form a solid dose formulation.

* * * * *